United States Patent [19]

Hanz et al.

[11] Patent Number: 4,692,625
[45] Date of Patent: Sep. 8, 1987

[54] DETECTOR HEAD MOUNTING MECHANISM AND SUPPORTING STRUCTURE

[75] Inventors: George J. Hanz, Bloomingdale, Ill.; Guenter Jung, Roettenbach; Michael Pflaum, Aisch, both of Fed. Rep. of Germany

[73] Assignee: Siemens Gammasonics, Inc., Des Plaines, Ill.

[21] Appl. No.: 747,731

[22] Filed: Jun. 24, 1985

[51] Int. Cl.<sup>4</sup> ............................................... G01T 1/20
[52] U.S. Cl. .................................................. 250/363 R
[58] Field of Search ....... 250/363 S, 363 SC, 363 SF; 378/189

[56] References Cited

U.S. PATENT DOCUMENTS

| 4,216,381 | 8/1980 | Lange | 250/363 SC |
| 4,438,335 | 3/1984 | Meeder | 250/363 SC |
| 4,459,485 | 7/1984 | Span | 250/363 SC |

FOREIGN PATENT DOCUMENTS 0154388 12/1979 Japan .............................. 250/363 SF Primary Examiner—Janice A. Howell
Assistant Examiner—David P. Porta
Attorney, Agent, or Firm—Mark H. Jay

[57] ABSTRACT

A mechanism for mounting a detector head including a collimator which comprises a supporting structure having a single trunnion axis for the detector head. A shifting mechanism is provided for shifting the detector head and the supporting structure with respect to each other in a manner that the detector head including the collimator is balanced with respect to the single trunnion axis. For overall balancing purposes the supporting structure also comprises a counterweight for the detector head secured to a detector head support arm and a device for varying the position of the center of gravity of the counterweight with respect to a joint moveably supporting the arm.

25 Claims, 12 Drawing Figures

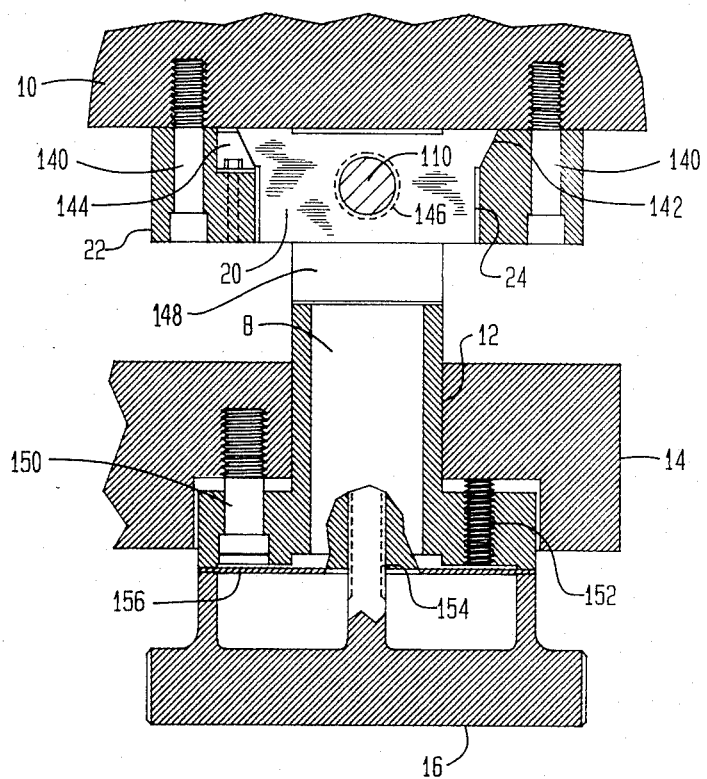

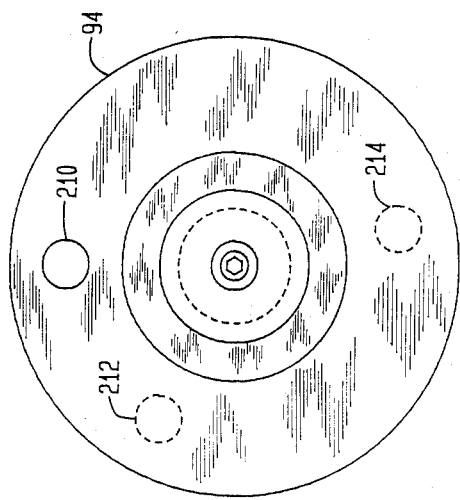
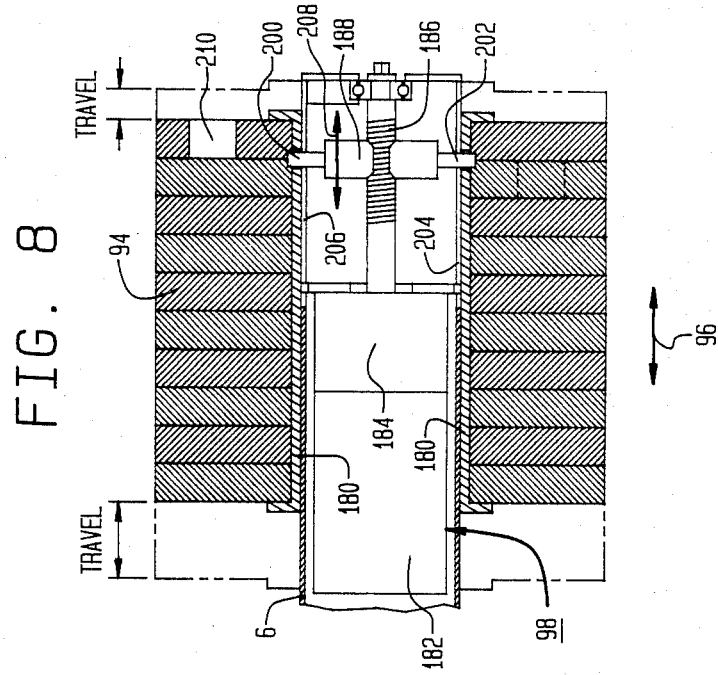

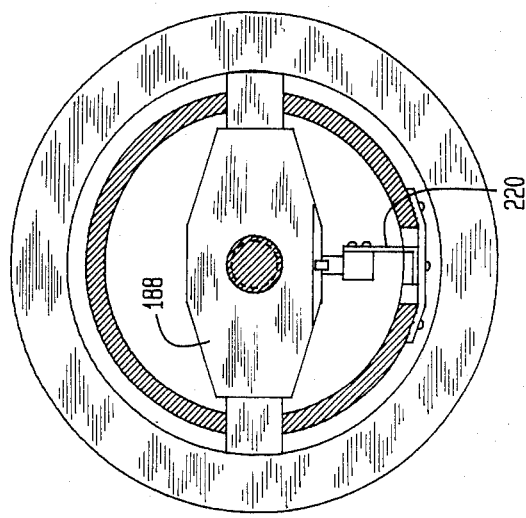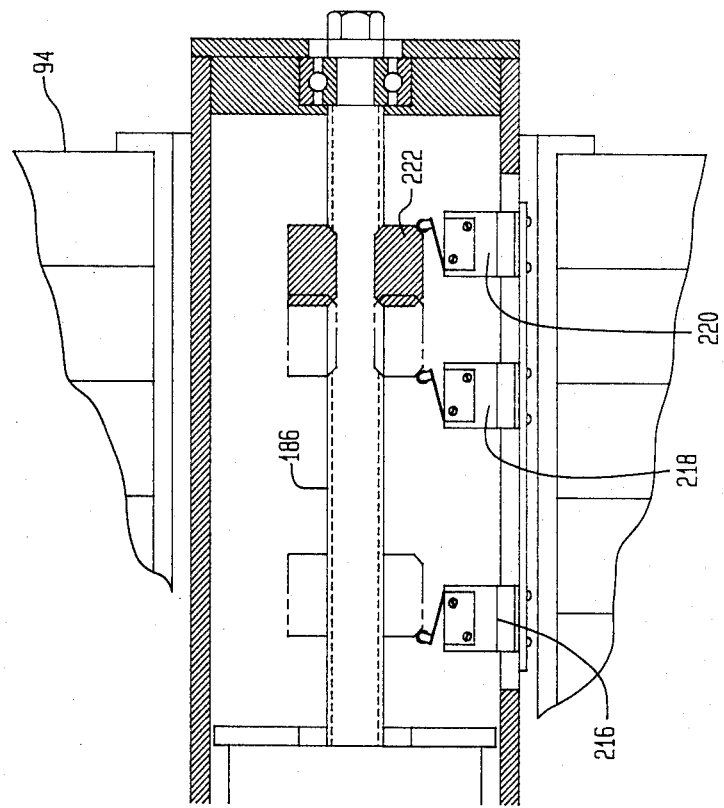

DETECTOR HEAD MOUNTING MECHANISM AND SUPPORTING STRUCTURE

BACKGROUND OF THE INVENTION

1. Field of the Invention

The present invention relates to a mechanism for mounting a detector head including a collimator onto a supporting structure of a radiation detector. The detector head is for example, a camera head of an Anger-type scintillation gamma camera or an x-ray detector head of an x-ray detecting device.

2. Description of the Prior Art

The choice of collimator to be used with a detector head of a radiation detector, in particular for medical diagnostic procedures, depends on the energy level of the radiation. Low energy collimators, for example, may be approximately 80 lbs. lighter than medium energy collimators. Due to that the detector head, which is pivotally mounted onto the supporting structure of the radiation detector, has to be balanced for collimators with different weights with respect to different pivot axes.

U.S. Pat. No. 4,438,335 (Meeder) describes a detector head mounting apparatus, wherein for balancing purposes and dependent on the weight of a collimator a selection is made between at least two different trunnion axes on the detector head in a manner that rotation of the head together with the collimator attached to the head occurs about the trunnion axis which passes nearest to the center of gravity of the head and collimator.

A similar detector head mounting mechanism is depicted in the commonly-owned patent application Ser. No. 555,100, entitled "Detector Head Mounting Mechanism" filed on Nov. 25, 1983 by Anatoly I. Gosis and Frank J. Bartos.

The Japanese laid-open patent application No. 54-154388 (Suzuki) illustrates a detector head mounting mechanism for a scintillation camera, which comprises a shiftable balance weight inside the detector head to match the centroid of the detector head to the center of rotation for collimators having different weights.

U.S. Pat. Nos. 4,101,779 (Schmedemann) and 4,365,343 (Grady et al.) finally describe x-ray apparatus wherein up and down movements of an x-ray source are balanced by shifting of suitable balance weights.

SUMMARY OF THE INVENTION

1. Objects

It is an object of this invention to provide for a technically simple overall balanced structure supporting a detector head including collimators having differing weights.

It is another object of this invention to provide for an improved mechanism for mounting a detector head including a collimator onto a supporting structure in a manner that balance changes due to differing collimator weights are accurately compensated with respect to a single trunnion axis of the detector head without utilizing additional balancing weights to match the centroid of the detector head to the center of rotation.

It is still another object of this invention to provide for an improved structure for supporting a detector head including a collimator on a joint in a manner that balance changes due to differing collimator weights are accurately compensated with respect to the joint.

2. Summary

According to this invention, an improved mechanism for mounting a detector head including a collimator is provided which comprises (a) a supporting structure supporting the detector head including the collimator, said supporting structure having a single trunnion axis for the detector head;

(b) a shifting means connected between detector head and supporting structure for shifting the detector head including the collimator and the supporting structure with respect to each other in a manner that the detector head including the collimator is balanced with respect to the single trunnion axis.

Also according to this invention an improved structure for supporting a detector head including a collimator is provided which comprises (a) an arm having one end supporting the detector head including the collimator and having another end supporting a counterweight for the detector head including the collimator, said counterweight having a center of gravity;

(b) a base;

(c) a joint mounted on the base and moveably supporting the arm; and (d) means connected to the counterweight for varying the position of the center of gravity of the counterweight with respect to the joint.

This invention provides for an accurate balancing of a detector head according to different collimator weights with respect to a single trunnion axis of the head. It also provides for an accurate balancing of the detector head with respect to the joint mounted on a base and moveably supporting the arm, which supports the detector head. Under these circumstances, a technically simple overall balanced structure supporting a detector head including collimators with differing weights is provided by this invention.

The foregoing and other objects, features and advantages of the invention will be apparent from the following more particular description of a prefered embodiment of the invention, as illustrated in the acompanying drawings.

BRIEF DESCRIPTION OF THE DRAWINGS

In the drawings:

FIG. 4 is the shifting mechanism of FIG. 2 in an enlarged cross section;

FIG. 8 is a first embodiment of a counterweight shifting mechanism according to this invention in a longitudinal section;

FIG. 9 is the mechanism of FIG. 8 in a top view;

FIG. 10 is a counterweight shifting mechanism comprising position switches;

FIG. 11 is the mechanism of FIG. 10 in a top view; and

DETAILED DESCRIPTION OF THE PREFERRED EMBODIMENTS

Figure 1:
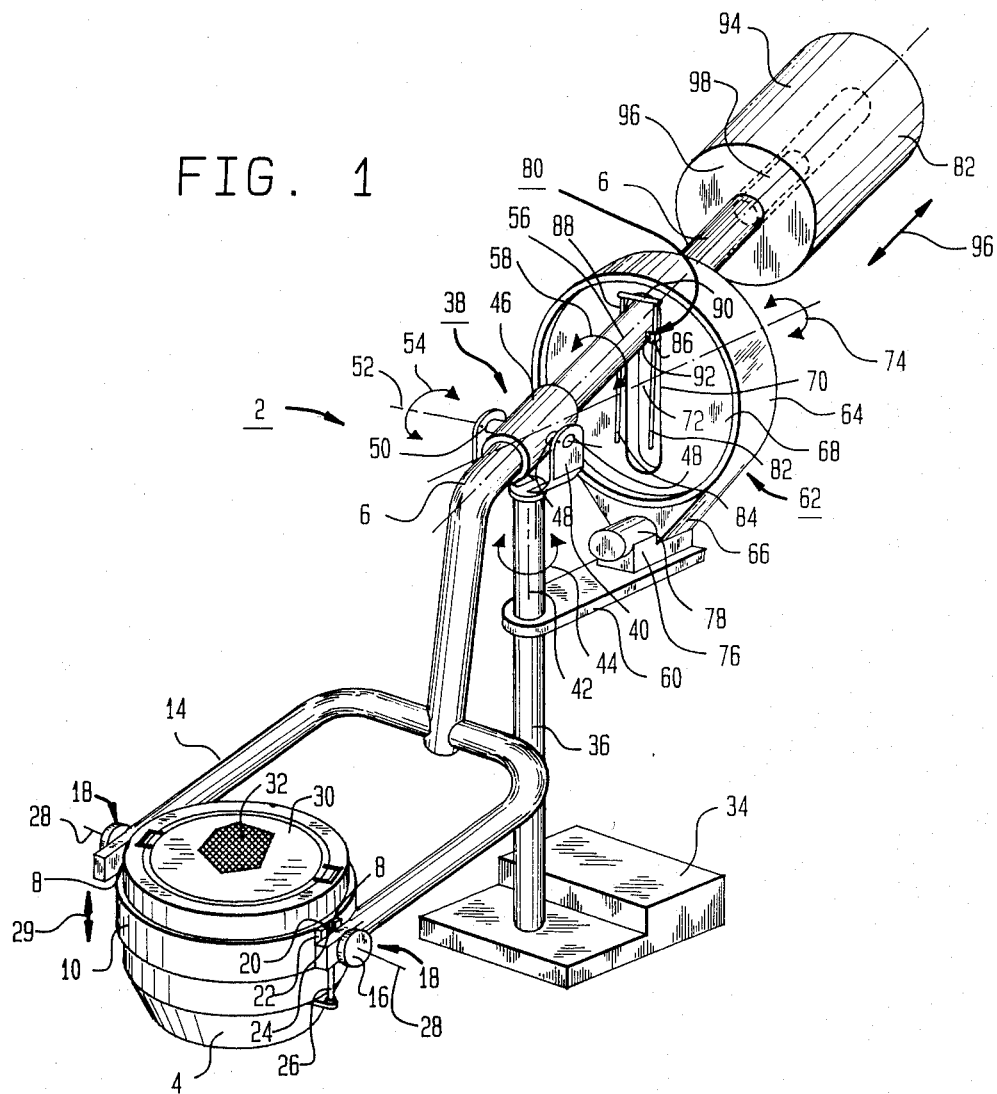
FIG. 1 is an overall perspective view of a gamma camera comprising supporting structure according to this invention.

FIG. 1 illustrates an Anger-type scintillation gamma camera 2 for emission computerized tomography (ECT) comprising a camera head 4 which is pivotably mounted on a bent end of a support arm 6 by means of trunnion pintals 8 of a trunnion ring 10. The trunnion pintals 8 are received in eyes 12 (see FIG. 4) of a yoke portion 14 of the support arm 6. A clamp 16 is provided for clamping each trunnion pintal 8 in its eye 12 of yoke portion 14.

As is indicated in FIG. 1 each trunnion pintal 8 is mounted to the trunnion ring 10 by means of a detector head shifting mechanism 18. As will later be described in more detail each mechanism 18 comprises for each of the bifurcated ends of the yoke portion 14 of the support arm 6 a threaded dove tail slider 20 and a slider housing 22. Each threaded dove tail slider 20 is slidably inserted in an opening 24 of the associated slider housing 22. Each slider housing 22 is secured to the trunnion ring 10 and each trunnion pintal 8 is secured to an associated threaded dove tail slider 20. By shifting the slider housing 22 and slider 20 with respect to each other by means of a screw drive 26 the camera head 4 is shifted with respect to the stable single trunnion axis 28 in directions of double arrow 29.

Under these circumstances, it is possible to compensate a change in balance of camera head 4 with respect to trunnion axis 28, in case collimators having differing weights are secured to the camera head 4.

In FIG. 1, for example, a low energy collimator 30 is attached to camera head 4 and the camera head 4 including collimator 30 is balanced with respect to single trunnion axis 28.

In case a heavier collimator, such as for example a medium energy collimator, is attached to the camera head 4, the camera head 4 has to be shifted by means of shifting mechanism 18 with respect to trunnion axis 28 in a manner that the balance change due to the higher collimator weight is accurately compensated.

Collimator 30 comprises collimator apertures which are indicated with the reference numeral 32 in FIG. 1.

As is also illustrated in FIG. 1 the support arm 6 is moveably mounted to a base 34 by means of a stanchion 36 and a three axis gimbal 38 on top of the stanchion 36. The gimbal 38 provides for a joint for the support arm 6. It comprises an U-shaped piece 40 which is rotatable on top of the stanchion 36 about vertical axis 42 in the directions of rotational arrow 44. The gimbal 38 further includes a sleeve member 46 mounted in the U-shaped piece 40 by means of trunnions 48, 50 such that it is rotatable about horizontal axis 52 in the directions of rotational arrow 54. The support arm 6 is inserted in the sleeve member 46 so that it is rotatable within the sleeve member about longitudinal arm axis 56 in the directions of rotational arrow 58.

The stanchion 36 further comprises a mounting plate 60 on which a frame 62 is mounted. The frame 62 includes an annular frame portion 64 and a basic frame portion 66. A circular slotted member 68 having a guidance slot 70 is inserted in annular frame portion 64 so that it is rotatable in the annular frame portion 64 about rotational axis 72 in the directions of rotational arrow 74. The basic frame portion 66 includes a mounting support 76 for mounting frame 62 on the mounting plate 60 on the one hand and for mounting a motor drive 78 on top of the mounting support 76 on the other hand.

The motor drive 78 is provided for rotating the circular slotted member 68 in the annular frame portion 64 about axis 72. The rotational axis 72 intersects the longitudinal arm axis 56 in the joint provided by the gimbal 38.

The support arm 6 is mounted in the guidance slot 70 of the slotted member 68 in a predetemined distance from the rotational axis 72 freely slidable along its longitudinal arm axis 56, however non-rotatably fixed with respect to the guidance slot 70. A special mounting mechanism for that purpose is indicated in FIG. 1 with the reference numeral 80. The mounting mechanism 80 comprises a first and second acme screws 82, 84 and a first and second nuts 86, 88 slidably mounted on the screws 82, 84, respectively. The first and second screws 82, 84 are tiltably secured with the one ends to the slotted member 68 by means of a tilting bar 90. The other ends of the first and second screws 82, 84 are freely movable. The first and second nuts 86, 88 are firmly connected with the support arm 6 by means of turnable pins 92. By synchronously rotating screws 82, 84 by means of a motor drive (not shown), nuts 86, 88 move up or down depending on the direction of rotation and the support arm 6 is shifted into the predetermined distance.

The element 94 in FIG. 1 is a counterweight for balancing the weight of the camera head 4 including collimator 30 with respect to joint 38. In this embodiment the counterweight 94 for example is cylindrical. Therefore, the counterweight 94 is symmetrical with respect to rotation about longitudinal arm axis 56, which is advantageous, since it prevents undesired torques during rotation of the counterweight when rotating the support arm 6 about its longitudinal arm axis 56. However, otherwise shaped counterweights, also non-symmetrical ones, can be utilized, if desired.

In FIG. 1, the counterweight 94 is mounted on the support arm 6 in a manner that is shiftable along the support arm 6 in the directions of double arrow 96. Shifting could be done manually; however, in the subject case, a motor drive is provided as indicated in FIG. 1 by reference numeral 98 for automatically shifting the counterweight 94. More details will later be described in connection with FIGS. 8-12.

Due to the shifting, the center of gravity of the counterweight 94 is tuned with respect to joint 38. As a result balance changes caused by differing collimator weights attached to camera head 4 can very easily and accurately be compensated with respect to joint 38.

Under these circumstances, a technically simple and accurately overall balanced structure for supporting a camera head 4 including collimators with differing weights has been provided by this invention. This is particularly advantageous for ECT diagnosis, since the camera head has to be extremely accurately positioned for ECT, while orbiting about a patient under examination.

Orbiting is caused by rotating the circular slotted member 68 in the annular frame portion 64 of frame 62 by means of motor drive 78. Due to this the support arm 6 is driven about the joint provided by the gimbal 38 on top of the stanchion 36 so that the camera head 4 traverses an arc with the camera head's active surface facing inward and so that a reference line drawn from the joint 38 to the camera head describes a conical surface having the joint 38 in its apex and the arc at its base. The radius of the arc is determined by the distance of the support arm 6, i.e. its longitudinal arm axis 56, from the rotational axis 72 of the circular slotted member 68.

Figure 2:
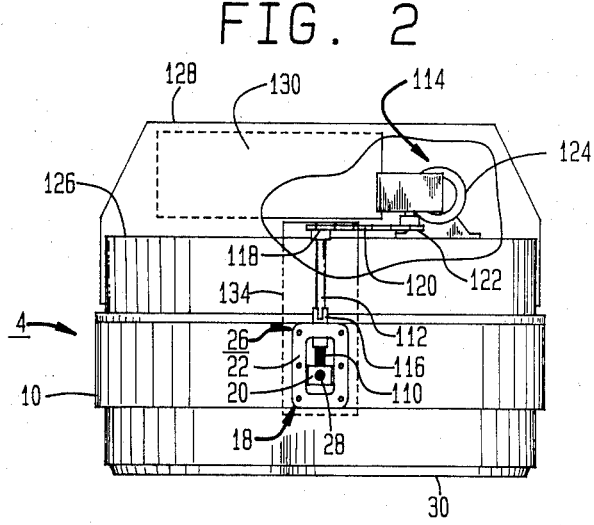
FIG. 2 is a gamma camera head comprising a shifting mechanism according to this invention in a side view.

FIG. 2 illustrates the camera head 4 of FIG. 1 in a side view. As can be seen from FIG. 2 in more detail the screw drive 26 of the shifting mechanism 18 comprises a screw 110, a shaft 112 and a motor drive 114 for rotating the screw 110 through shaft 112. The screw 110 is threadably connected with the threaded dove tail slider 20. Shaft 112 is coupled with one end to screw 110 by means of a coupling member 116 in a manner that a detachable coupling is provided between shaft and screw. The other end of shaft 112 comprises a sprocket 118 which is connected through a chain 120 with the drive sprocket 122 of a gear motor 124 of the motor drive 114.

In the embodiment of FIG. 2 the gear motor 124 is mounted on top of a cover 126 for the photomultiplier tubes (not shown) of the camera head 4 inside an outer housing cover 128 of the camera head which also contains the processor electronic 130.

Figure 3:
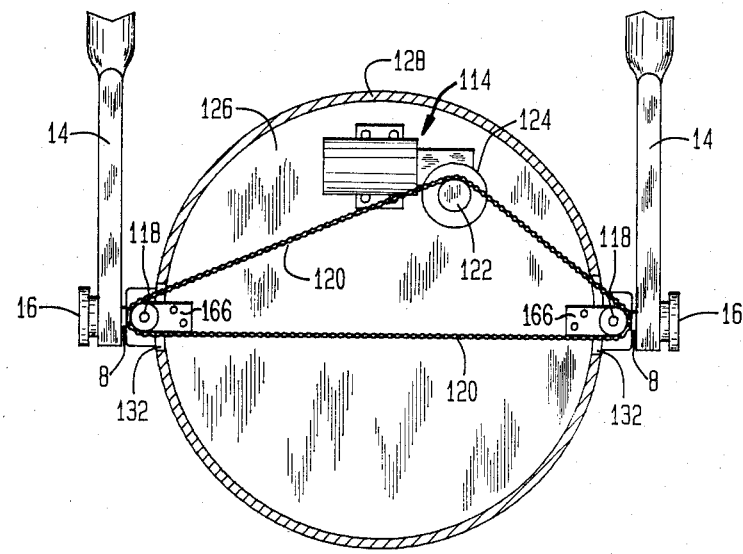
FIG. 3 is the head of FIG. 2 in a partially cross-sectional top view.

As indicated in the cross sectional view of FIG. 3 the outer housing cover 128 comprises a slot 132 on each diametrically opposite side of the housing of the camera head 4 which provides for an access of chain 120 from sprockets 118 outside the outer housing cover 128 to the drive sprocket 122 of the gear motor 124 inside the outer housing cover 128.

As is also depicted in FIG. 2 each shifting mechanism 18 and each associated screw drive 26 on each side of the camera head 4 are covered by a protective (metal or plastic) cover 134.

FIG. 4 shows a shifting mechanism 18 in an enlarged cross section. According to FIG. 4 the slider housing 22 is secured to the trunnion ring 10 by means of fastening screws 140. The dimensions of the opening groove 24 of each slider housing 22 is formed by a fixed gib 142 and an adjustable gib 144. Each threaded dove tail slider 20 includes threaded hole 146 for screw 110. The slider 20 is an integrated part of an associated trunnion pintal 8 which is inserted in an eye 12 of the bifurcated ends of the yoke portion 14 by means of an axially adjustable bushing 148 shaped in a manner as illustrated in FIG. 4. The bushing 148 is secured and axially adjusted with respect to the bifurcated ends by means of fastening screws 150 and axial adjustment screws 152. Each clamp 16 which can be screwed into threaded hole 154 of the trunnion pintals 8 comprises a clamp disc 156 which provides for a clamping force between clamp 16 and trunnion pintals 8.

Figure 5:
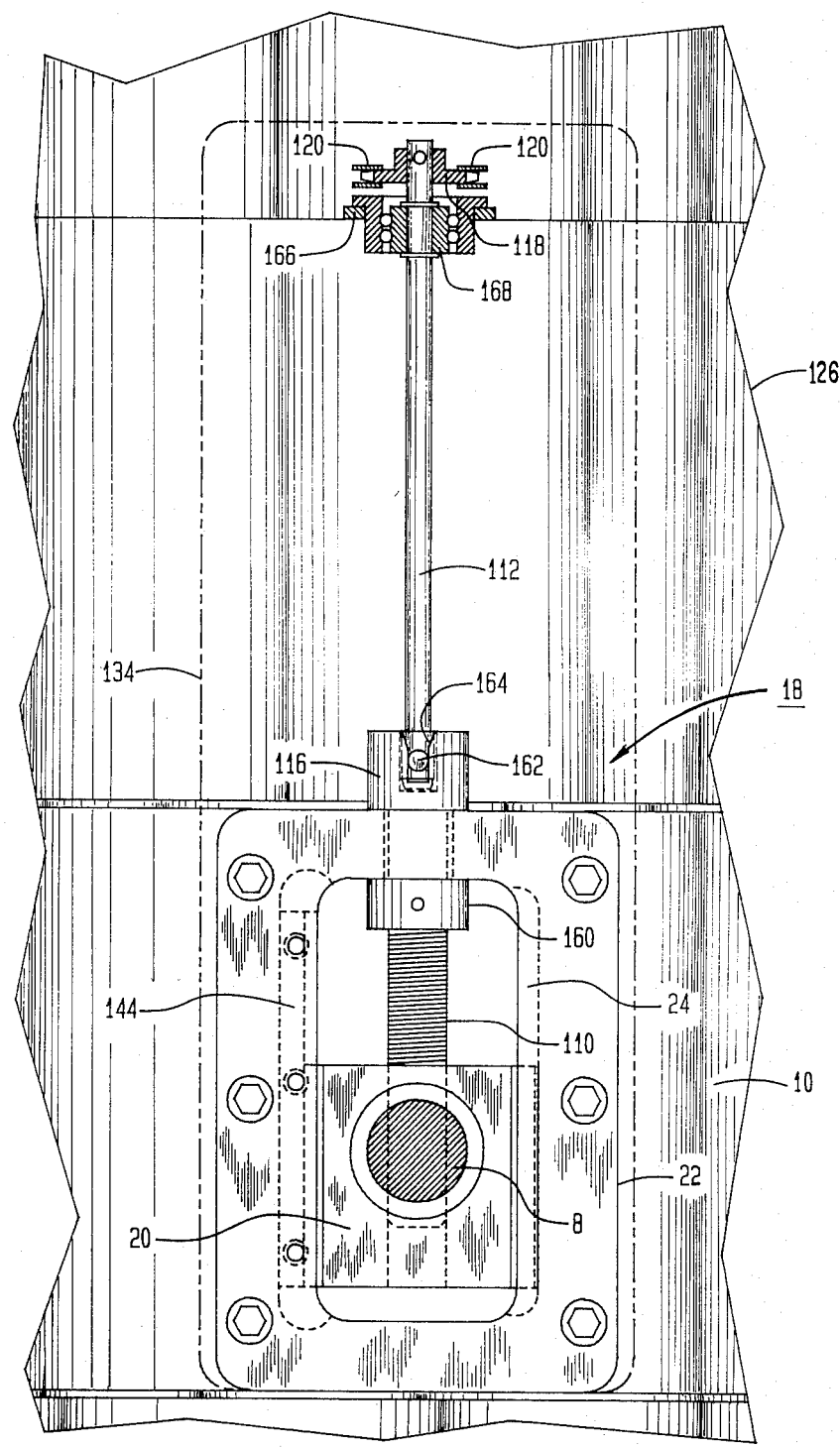
FIG. 5 is the shifting mechanism of FIG. 2 in an enlarged side view.

FIG. 5 illustrates an enlarged side view of the detector head shifting translation mechanism 18. The element 160 is a bearing collar and the element 162 is a pin secured to shaft 112. Pin 162 detachably engages a slot 164 in the coupling member 116. In case the outer housing cover 128 and the cover 126 are removed, the shaft 112 is decoupled from screw 110. Under these circumstances, a very simple coupling or decoupling of the screw 110 with or from the motor drive 114 is provided dependent on whether or not the outer housing cover 128 and the cover 126 are mounted. The upper end of shaft 112 is secured to the cover 126 by means of a mounting plate 166 and a bearing 168.

Figure 7:
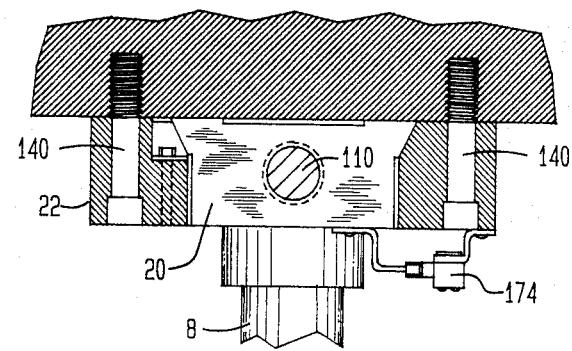
FIG. 7 is a top view of FIG. 6.
Figure 6:
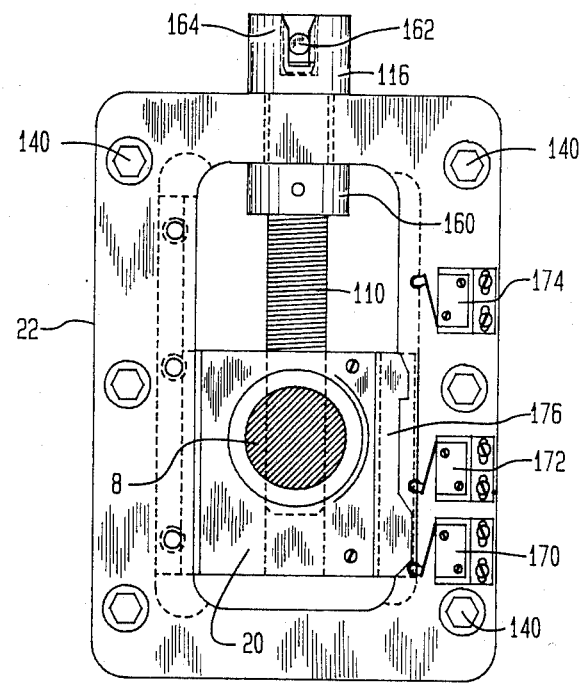
FIG. 6 is the shifting mechanism of FIG. 2 comprising position switches.

FIGS. 6 and 7 illustrate a shifting mechanism 18 which comprises an arrangement of position switches 170, 172, 174 and a switch actuator cam 176. The position switches 170–174 are secured to the slider housing 22 and the switch actuator cam 176 is mounted on the slider 20. Each switch in combination with the cam provides for a switch signal which stops rotation of the gear motor 124 in case a collimator having a special weight has been attached to the camera head 4. The collimator type is thereby signaled to an associated switch in a conventional manner by means of optical markers for example. Under these circumstances, the camera head is always automatically balanced depending on the differing weight of the collimator.

FIGS. 8 and 9 depict a first embodiment of a counterweight shifting mechanism. The counterweight 94 is mounted on a sleeve 180 which is slidably secured on the support arm 6. The motor drive 98 inside the support arm 6 comprises a motor 182 and a speed reducer 184. A screw 186 is rotated by motor drive 98. A nut 188 is slidably mounted on the screw 186. The nut 188 is secured by means of pins 200, 202 to the counterweight 94 through slots 204 and 206 in the support arm 6. When rotating the screw 186 in the one or the other direction the nut 188 moves in one or the other direction of double arrow 208. As a result, the counterweight 94 is shifted in the one or the other direction of double arrow 96, as has been previously described in connection with FIG. 1.

The elements indicated with 210, 212, 214 are holes in the counterweight 94. These holes (removed material) balance a possible decentral imbalance of the camera head 4 along trunnion axis 28 between the bifurcated ends of the yoke portion 14 of the support arm 6.

FIGS. 10 and 11 illustrate a counterweight shifting mechanism comprising an arrangement of position switches 216, 218, 220 and a switch actuator cam 222 which work similarly to that of FIGS. 6 and 7 for automatically balancing the counterweight with respect to joint 38.

Figure 12:
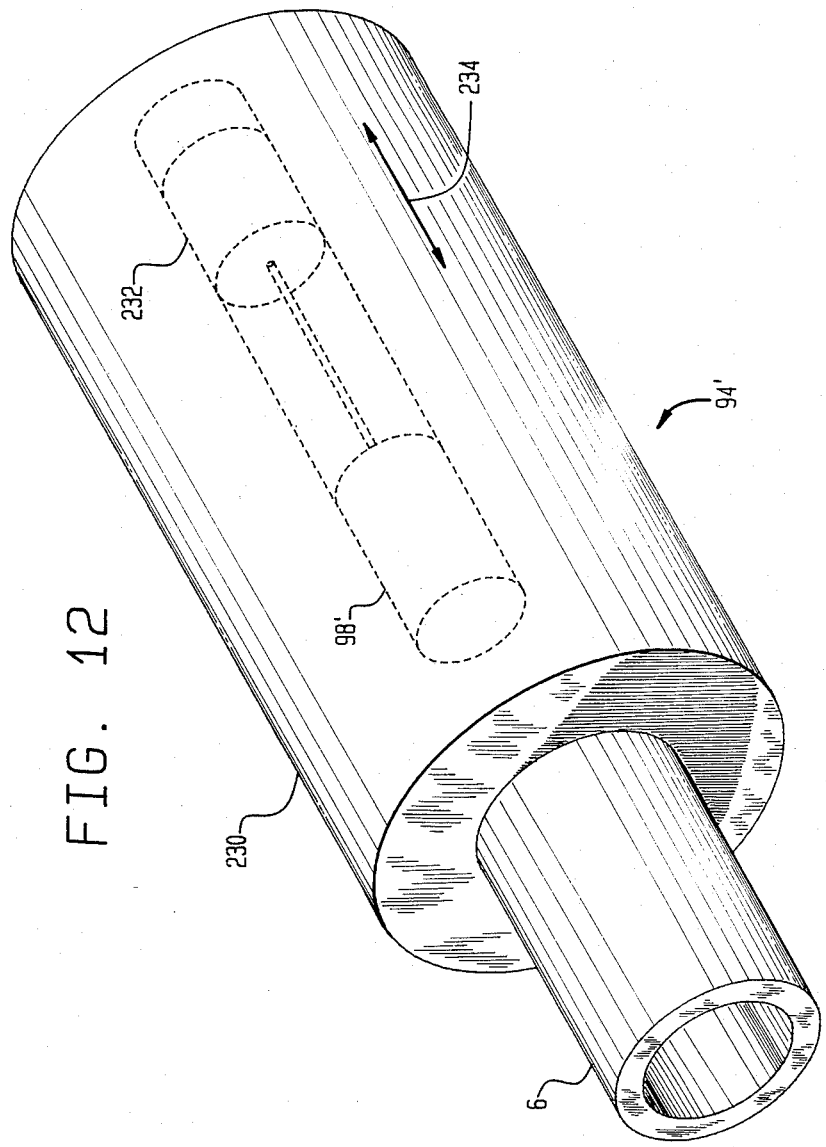
FIG. 12 is a second embodiment of a counterweight shifting mechanism.

FIG. 12 shows a second embodiment of a counterweight shifting mechanism. As indicated, the counterweight 94' comprises a first counterweight portion 230 and a second counterweight portion 232. The first counterweight portion 230 is fixed on the support arm 6. The second counterweight portion 232 is slidably inserted inside the first counterweight portion 230. The second counterweight portion 232 can be shifted by means of motor drive 98' inside the first counterweight portion 230 in directions of double arrow 234. As a result, the counterweight 94' can be balanced with respect to joint 38.

Having thus described the invention with particular reference to the preferred forms thereof, it will be obvious to those skilled in the art to which the invention pertains, after understanding the invention, that various changes and modifications may be made therein without departing from the spirit and scope of the invention as defined by the claims appended hereto.

What is claimed is:

1. A mechanism for mounting a detector head including a collimator, comprising:
    (a) a supporting structure supporting the detector head including the collimator, said supporting structure having a single trunnion axis for the detector head;
    (b1) a shifting means for shifting the detector head including the collimator and the supporting structure with respect to each other in a manner that the detector head including the collimator is balanced with respect to the single trunnion axis,
    (b2) the shifting means including a slider housing and a slider slidably inserted in the slider housing, wherein (b3) one is secured to the supporting structure in the single trunnion axis and the other one is secured to the detector head.

2. The mechanism according to claim 1, wherein the supporting structure further comprises:
(a) an arm having one end supporting the detector head including the collimator and having another end supporting a counterweight for the detector head including the collimator, said counterweight having a center of gravity;
(b) a base;
(c) a joint mounted on the base and moveably supporting the arm; and
(d) means connected to the counterweight for varying the position of the center of gravity of the counterweight with respect to the joint.

3. The mechanism according to claim 1, wherein the slider is secured to the supporting structure in the trunnion axis and the slider housing is secured to the detector head.

4. The mechanism according to claim 1, wherein the slider includes a thread and wherein the shifting means further comprises a rotatable screw screwably mounted in the slider thread in a manner that at a rotation of the screw slider and slider housing are shifted with respect to each other.

5. The mechanism according to claim 4, wherein the shifting means further comprises a motor drive for rotating the screw.

6. The mechanism according to claim 5, wherein the detector head comprises a housing and a housing cover and wherein the screw and slider are mounted outside and the motor drive is mounted inside the housing cover and wherein the cover contains an access for a transmission means connecting the motor drive inside with the screw outside the housing cover.

7. The mechanism according to claim 5, wherein the detector head comprises a photomultiplier tube inside the housing and a cover for the photomultiplier tube and wherein the motor drive is mounted on the cover for the photomultiplier tube and both the cover and the photomultiplier tube are covered by the housing cover.

8. The mechanism according to claim 8, wherein the screw is secured to the housing and wherein the shifting means further comprises a rotatable shaft being nondetachably secured to the cover on the one hand and being detachably connected with the screw on the other hand in a manner that when demounting the cover the shaft is decoupled from the screw.

9. The mechanism according to claim 8, wherein the shaft comprises a pin and the screw includes a slot and the pin engages the slot in a manner that shaft and screw are detachably coupled with each other.

10. The mechanism according to claim 1, wherein the slider housing comprises an opening for insertion of a dove tail slider.

11. The mechanism according to claim 10, wherein the dimensions of the opening are formed by a fixed first gib and an adjustable second gib.

12. A mechanism according to claim 2, wherein the means for varying the position of the center of gravity comprises a sliding means for slidably mounting the counterweight on the support arm along the longitudinal arm axis.

13. A mechanism according to claim 12, wherein the means for varying the position of the center of gravity further comprises a motor drive for shifting the counterweight along the longitudinal arm axis.

14. A mechanism according to claim 13, wherein the motor drive is mounted inside the support arm.

15. A mechanism according to claim 2, wherein the counterweight comprises a first and second portions and wherein the means for varying the position of the center of gravity contains means for shifting both portions with respect to each other in a manner that the center of gravity is changed.

16. A mechanism according to claim 15, wherein the first counterweight portion is put on the support arm at the arm end supporting the counterweight and the second counterweight portion is slidably inserted in the first counterweight portion.

17. A mechanism according to claim 16, wherein the second counterweight portion is slidably inserted inside the support arm.

18. A mechanism according to claim 15, wherein the means for shifting the first and second portions with respect to each other comprises a motor drive.

19. A mechanism according to claim 18, wherein the motor drive is inserted in the first counterweight portion.

20. A mechanism according to claim 18, wherein the motor drive is inserted inside the support arm.

21. A mechanism for mounting a detector head including a collimator comprising:
(a) a supporting structure supporting the detector head including the collimator, said supporting structure containing
(a1) an arm having a yoke portion at its distal end, said yoke portion including two bifurcated ends; and
(a2) a trunnion ring bearing the detector head including the collimator, said trunnion ring having a first and second trunnion pintals rotatably secured between the two bifurcated ends of the yoke portion in a manner that both trunnion pintals in conjunction form a single trunnion axis; and
(b) a trunnion ring shifting means connected between the trunnion ring and each first and second trunnion pintals for shifting the trunnion ring containing the detector head and the collimator with respect to the first and second trunnion pintals forming a single trunnion axis in a manner that the detector head including the collimator is balanced with respect to the single trunnion axis.

22. The mechanism according to claim 21, wherein the trunnion ring shifting means comprises for each first and second trunnion pintle a slider housing and a slider slidably inserted in the slider housing, wherein one is secured to the trunnion ring and the other one is secured to the associated first and second trunnion pintal.

23. The mechanism according to claim 22, wherein each slider is secured to an associated first and second pintal and the associated slider housing is secured to the trunnion ring.

24. The mechanism according to claim 23, wherein each slider is an integrated part of its associated trunnion pintal.

25. The mechanism according to claim 23, wherein each slider includes a thread and wherein the trunnion ring shifting means further comprises for each threaded slider a rotatable screw mounted screwably along the thread in a manner that each slider and slider housing are shifted with respect to each other.

* * * * *